United States Patent [19]

Dugan et al.

[11] 4,238,467

[45] Dec. 9, 1980

[54] METHOD OF PRODUCING YTTRIUM OXIDE WITH PARTICULARLY BIG PARTICLES

[76] Inventors: Martin Dugan, Bakke Soendre 81, 2040 Kloefta; Norvald Gjelsvik, Fossumkroken 13, Oslo 9, both of Norway

[21] Appl. No.: 28,237

[22] Filed: Apr. 9, 1979

[30] Foreign Application Priority Data

Apr. 14, 1978 [NO] Norway .................................. 781301

[51] Int. Cl.$^3$ ............................................. C01F 17/00
[52] U.S. Cl. ..................................................... 423/263
[58] Field of Search ...................... 423/263; 260/429.2

[56] References Cited
FOREIGN PATENT DOCUMENTS 224106 9/1959 Australia ................................. 260/429.2

OTHER PUBLICATIONS

Moosath et al., "Zeit. fur anorg. und allgemeine Chemie", vol. 324, 1963, pp. 99–102.
Glasner et al., "Journal of Inorg. & Nuclear Chem.", vol. 25, 1963, pp. 1119–1127.
Vickery, "The Chemistry of Yttrium and Scandium", Pergamon Press, N.Y., 1960, pp. 100–101.

*Primary Examiner*—Herbert T. Carter
*Attorney, Agent, or Firm*—Eyre, Mann, Lucas & Just

[57] ABSTRACT

Yttrium oxide with particularly big particles is formed by reacting yttrium ions with oxalate ions so that yttrium oxalate is precipitated. The precipitated yttrium oxalate is maintained at a temperature of 90°–100° C. for a period from ½ to 24 hours for formation of a crystal form of yttrium oxalate which can be dried and ignited to oxide without disintergrating. The heat-treatment can be combined with the precipitation and also with the subsequent drying and ignition to yttrium oxide.

3 Claims, No Drawings

METHOD OF PRODUCING YTTRIUM OXIDE WITH PARTICULARLY BIG PARTICLES

Usual commercial yttrium oxide has a particle size of between 1 and 20$\mu$. This oxide consists however of very uneven particles and it is therefore difficult to feed out from bins etc. as it will form lumps so that the material does not flow in an even flow. The powder will further pack poorly so that the material often has a bigger volume than necessary. This is especially of importance in cases where yttrium oxide shall be melted and where it is desired to fill as much oxide as possible in a crucible of a certain size.

Yttrium oxide is usually produced by precipitating yttrium oxalate by reacting a solution of yttrium ions and oxalate ions in solid or dissolved state. Even if there by the precipitation is obtained big well-shaped crystals of yttrium oxalate these will by the directly following drying and ignition fall to pieces and give an oxide which has a smaller particle size than the precipitated oxalate. It is then obtained the above described oxide of particle size between 1 to 20$\mu$ consisting of uneven particles. By the method of the invention that precipitate which is formed when yttrium ions and oxalate ions are reacted, is maintained at a temperature of 90-100° C. for ½ to 24 hours. The oxalate will then be transformed to a new crystal form with more cubic shaped crystals which by ignition will not fall to pieces but chiefly keep their shape until the oxide production is finished. This will then give a possibility to adjust the particle size in the ready yttrium oxide by adjusting the particle size in the oxalate, which possibility only exists in a limited degree when normal oxalate is produced. It is thus not primarily the aim to increase the crystal size in the yttrium oxalate before the ignition, but to procure a crystal type which can be ignited to oxide without falling to pieces. Only to increase the crystal size by the very well known process to maintain the yttrium oxalate crystals hot for a certain period is thus not enough.

The new feature by the present method is that there simultaneously with the increase of the crystal size is effected a recrystallization to another crystal structure which has other and better characteristics than the one with which the production was started. By controlling the time for the heat-treatment the size of the particles in the ready oxide can to a certain degree be predetermined. It is by the method of the invention obtained particles sizes of 5-50$\mu$ simultaneously as the weight of the oxide powder is increased to 1,4 to 1,8 kg per liter in comparison to about 1 kg per liter for usual oxide. By use of the new oxide with big particles it has for instance been possible to fill up to 1,8 kg in a crucible of one litre volume while there by use of usual oxide only has been possible to fill about 1 kg into the same crucible. This is of big importance by melting of yttrium oxide as the capacity of one crucible will be increased to approximately the double. It has from the side of producers of TV-phosphorus for a long time been expressed a desire of being able to produce a yttrium oxide with bigger particle sizes and this desire is met by the method of the invention. It has also proved that it because of the adhering tendency is difficult to pelletize usual yttrium oxide on an automatic pelletizing equipment as the oxide does not flow in the feeding arrangement, but adheres to the walls and forms bridges and hollow spaces within the bins.

Yttrium oxide produced according to the new process has only negligible adhering tendency but flows even in any feeding equipment without any of those drawbacks which are connected to usual yttrium oxide. The new oxide can therefore be dosed and supplied automatically in an easy and exact way.

The heat-treatment can take place directly after the precipitation in the same or in a separate equipment without separating the crystals from the solution. It is also possible to separate the crystals from the solution and wash them and then carry out the recrystallization by combination with drying and calcining process. Other possibilities are also present, and any practical combination of precipitation, heat-treatment, drying and calcination which must be of advantage is covered by this invention.

The following examples of the method can be given. The particle size in the oxides are indicated in $\mu$ ($10^{-6}$).

EXAMPLE 1

A solution of yttrium nitrate containing 15 g Y/l was supplied with oxalic acid until approximately the complete contents of yttrium was precipitated as oxalate. The precipitate was divided into two parts. One part was directly washed, dried and ignited to oxide. The other part was maintained in the mother lye for 30 hours at 95°-100° C. The original crystals of oxalate in the heat-treated part of the precipitation were then recrystallized into another type of more cubic shape. The precipitate was then washed, dried and ignited to oxide. The particle size in the ready oxide was determined by sedimentation. The results are given in the following table:

| Treatment of oxalate | Weight % less than indicated size | | | | | | | | | |
|---|---|---|---|---|---|---|---|---|---|---|
| | 1$\mu$ | 2$\mu$ | 3$\mu$ | 5$\mu$ | 10$\mu$ | 15$\mu$ | 20$\mu$ | 30$\mu$ | 40$\mu$ | 50$\mu$ |
| None | 0 | 11 | 30 | 55 | 96 | | | | | |
| About 100° C. for 20 hours | | | 0 | 0 | 5 | 10 | 20 | 50 | 80 | 90 |

EXAMPLE 2

The yttrium oxalate was precipitated as in example 1, but this time the complete precipitate was washed. A part of it was supplied with water until a slurry was formed and kept at 95°-100° C. for 20 hours. It was then filtered, dried and ignited to oxide. Another part was directly dried and ignited to oxide. The distribution of particle size in the two oxides was as follows:

| Treatment of oxalate | Weight % less than indicated size | | | | | | | |
|---|---|---|---|---|---|---|---|---|
| | 1$\mu$ | 2$\mu$ | 3$\mu$ | 5$\mu$ | 10$\mu$ | 20$\mu$ | 30$\mu$ | 40$\mu$ |
| None | 0 | 10 | 30 | 57 | 99 | | | |
| About 100° C. for 20 hours | | | 0 | 2 | 33 | 67 | 95 | |

EXAMPLE 3

A solution of yttrium nitrate containing 15 g Y/l was supplied with ammonium oxalate until practically all the amount of the yttrium contents had been precipitated as oxalate. The precipitate was then treated as in example 2. The size distribution in the ready oxides was as follows:

| Treatment of oxalate | Weight % less than indicated size | | | | | | |
|---|---|---|---|---|---|---|---|
| | 1μ | 2μ | 3μ | 5μ | 10μ | 20μ | 30μ |
| None | 0 | 9 | 32 | 64 | 95 | | |
| About 100° C. for 20 hours | | 0 | 3 | 20 | 60 | 90 | |

EXAMPLE 4

Yttrium oxalate was produced and treated as in example 2, but this time samples was taken after respectively 2, 3 and 4 hours. The distribution of particles size in the ready oxides was as follows:

| Treatment of oxalate | Weight % less than indicated size | | | | | | |
|---|---|---|---|---|---|---|---|
| | 1μ | 2μ | 3μ | 5μ | 10μ | 20μ | 30μ |
| None | 0 | 9 | 27 | 58 | 95 | | |
| About 100° C. for 2 hours | 0 | 6 | 25 | 59 | 95 | | |
| About 100° C. for 3 hours | | 0 | 11 | 18 | 59 | 94 | |
| About 100° C. for 4 hours | | 0 | 1 | 4 | 47 | 91 | 95 |

EXAMPLE 5

A solution of yttrium nitrate containing 1 g Y/1 was precipitated with oxalic acid. The precipitate was distributed into three portions. One portion was washed and ignited to oxide No. 1. Another portion was washed, transferred to a slurry by means of water and kept at 95°–100° C. for 20 hours before it was ignited to oxide No. 2. The third portion is kept at 95°–100° C. for 20 hours in the mother lye. This part was then washed and ignited to oxide No. 3. The distribution of the particle size was as follows:

| Oxide No. | Weight % less than indicated size | | | | | | | | | |
|---|---|---|---|---|---|---|---|---|---|---|
| | 1μ | 2μ | 3μ | 5μ | 10μ | 15μ | 20μ | 30μ | 40μ | 50μ |
| 1 | 2 | 16 | 38 | 68 | 98 | | | | | |
| 2 | | | | | 0 | 3 | 7 | 24 | 55 | 92 |
| 3 | | | | | | 0 | 0,5 | 2 | 3 | 98 |

EXAMPLE 6

Yttrium oxalate was precipitated and treated as in example 5, but this time there was employed a solution which contained 50 g Y/1. The distribution of particle size in the ready oxides was as follows:

| Oxide No. | Weight % less than indicated size | | | | | | | | | |
|---|---|---|---|---|---|---|---|---|---|---|
| | 1μ | 2μ | 3μ | 5μ | 10μ | 15μ | 20μ | 30μ | 40μ | 50μ |
| 1 | 0 | 13 | 40 | 66 | 95 | | | | | |
| 2 | | | | 5 | 17 | 31 | 50 | 86 | 97 | |
| 3 | | | 8 | 20 | 32 | 34 | 35 | 40 | 65 | |

EXAMPLE 7

Yttrium oxalate was produced and treated as in example 1, but this time there was utilized a an yttrium chloride solution with 15 g Y/1. The distribution of particle size in the ready oxides was:

| Treatment of oxalate | Weight % less than indicated size | | | | | | |
|---|---|---|---|---|---|---|---|
| | 1μ | 2μ | 3μ | 5μ | 10μ | 20μ | 30μ |
| None | 0 | 10 | 38 | 72 | 96 | | |
| About 100° C. for 20 hours | 0 | 3 | 10 | 20 | 40 | 83 | 95 |

We claim:
1. A method of producing yttrium oxide particles with substantially all of the particles having a size greater than five microns comprising:
   (a) precipitating yttrium oxalate;
   (b) maintaining the yttrium oxalate in a liquid medium at a temperature of 90°–100° C. for at least three hours whereby yttrium oxalate crystals are formed;
   (c) drying the yttrium oxalate crystals;
   (d) calcining the yttrium oxalate crystals whereby the yttrium oxalate is converted to yttrium oxide.
2. The method of claim 1 wherein steps (a) and (b) are carried out simultaneously.
3. The method of claim 1 wherein steps (a)–(d) are carried out in one continuous process.

* * * * *